(12) United States Patent
Kotachi et al.

(10) Patent No.: US 7,642,385 B2
(45) Date of Patent: Jan. 5, 2010

(54) ALCOHOL COMPOUNDS

(75) Inventors: Shinji Kotachi, Wakayama (JP);
Shigeyoshi Tanaka, Wakayama (JP);
Satoshi Ohno, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 12/306,430

(22) PCT Filed: Jun. 21, 2007

(86) PCT No.: PCT/JP2007/062482

§ 371 (c)(1),
(2), (4) Date: Dec. 23, 2008

(87) PCT Pub. No.: WO2008/001668

PCT Pub. Date: Jan. 3, 2008

(65) Prior Publication Data

US 2009/0182177 A1    Jul. 16, 2009

(30) Foreign Application Priority Data

Jun. 26, 2006    (JP) .............................. 2006-174994

(51) Int. Cl.
C07C 35/18 (2006.01)
A61K 8/18 (2006.01)
(52) U.S. Cl. ........................................ 568/825; 512/22
(58) Field of Classification Search ................. 568/825; 512/22
See application file for complete search history.

(56) References Cited

U.S. PATENT DOCUMENTS

| 3,993,604 A | 11/1976 | Thomas et al. |
| 4,306,099 A | 12/1981 | Fetizon et al. |
| 4,719,105 A * | 1/1988 | Schleppnik ............... 424/76.21 |

FOREIGN PATENT DOCUMENTS

| JP | 50 35351 | 4/1975 |
| JP | 55 020755 | 2/1980 |
| JP | 58 131927 | 8/1983 |
| JP | 2001 031608 | 2/2001 |
| WO | 2005 030914 | 4/2005 |
| WO | 2005 030915 | 4/2005 |

OTHER PUBLICATIONS

Blomquist, A. T. et al., "Terpene-Formaldehyde Reactions. I. α-Terpinene", J. Org. Chem., vol. 32, No. 12, pp. 3986-3989, (1967).

* cited by examiner

*Primary Examiner*—Sikarl A Witherspoon
(74) *Attorney, Agent, or Firm*—Oblon, Spivak, McClelland, Maier & Neustadt, L.L.P.

(57) ABSTRACT

The present invention relates to alcohol compounds having a scent of natural lily of the valley substantially without any woody scent limiting their applications to raw materials of perfume preparations, and a process for producing the alcohol compounds. The alcohol compounds are represented by the following general formula (I):

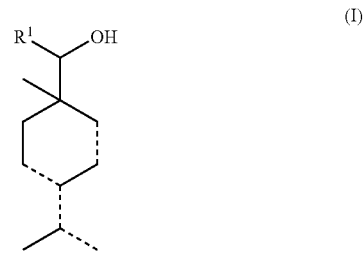

wherein $R^1$ is a hydrogen atom or a hydrocarbon group having 1 to 4 carbon atoms; and any one of dotted lines represents a double bond, and the remaining three dotted lines each represent a single bond.

5 Claims, No Drawings

ALCOHOL COMPOUNDS

FIELD OF THE INVENTION

The present invention relates to alcohol compounds that are useful as raw materials for perfume preparations, a process for producing the alcohol compounds, and perfume compositions containing the alcohol compounds.

BACKGROUND OF THE INVENTION

It is conventionally known that cyclohexyl alkanols having a carbon-to-carbon double bond include many perfume compounds having a floral odor. For example, it is known that 4-isopropenylcyclohexylmethanol has a scent reminiscent of a blossom of lily of the valley (refer to Patent Document 1). In addition, it is also known that cyclohexyl alkanols have a voluminous floral odor, or cyclohexylmethanols have a voluminous floral odor (refer to Patent Documents 2 and 3). However, these compounds have woody side notes and, therefore, are unfavorable for reproducing the scent of lily of the valley, and further have such a problem that they can be used in perfume preparations only in a limited amount.

Further, there are known examples of synthesis of 4-isopropenyl-1-methyl cyclohexa-2,4-dienylmethanol or 4-isopropylidene-1-methyl-2-cyclohexenylmethanol (Non-Patent Document 1). However, in the Non-Patent Document 1, there is no description concerning a odor of these compounds. Therefore, it is not known that these alcohol compounds are useful as perfumes.

Patent Document 1: JP 50-35351A

Patent Document 2: JP 2000-169409A

Patent Document 3: JP 2000-302712A

Non-Patent Document 1: "The Journal of Organic Chemistry", Vol. 32, pp. 3986 to 3989 (1967)

SUMMARY OF THE INVENTION

The present invention relates to alcohol compounds having a scent of natural lily of the valley substantially without any woody scent limiting their applications to raw materials of perfume preparations, a process for producing the alcohol compounds, and perfume compositions containing the alcohol compounds.

As a result of synthesis of various alcohol compounds and extensive researches and studies on odors thereof, the present inventors have found that the compounds having a six-membered ring hydrocarbon skeleton in which a methyl group is bonded to the alkanol group-bonded carbon atom, or a mixture of the compounds, not only exhibit a scent of natural lily of the valley as aimed by the present invention substantially without any undesirable woody scent, but also have a fresh floral odor and an excellent persistency of the fragrance.

Thus, the present invention relates to an alcohol compound, a process for producing the alcohol compound, and a perfume composition containing the alcohol compound, as described below.

1. An alcohol compound represented by the following general formula (I):

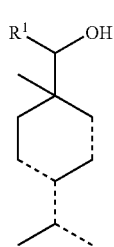

(I)

wherein $R^1$ is a hydrogen atom or a hydrocarbon group having 1 to 4 carbon atoms; and any one of dotted lines represents a double bond, and the remaining three dotted lines each represent a single bond.

2. A process for producing the alcohol compound represented by the general formula (I), which includes the step of subjecting a compound represented by the following general formula (II) to reduction reaction:

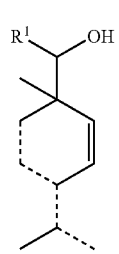

(II)

wherein $R^1$ is a hydrogen atom or a hydrocarbon group having 1 to 4 carbon atoms; and any one of dotted lines represents a double bond, and the remaining three dotted lines each represent a single bond.

3. A perfume composition including an alcohol compound represented by the following general formula (III):

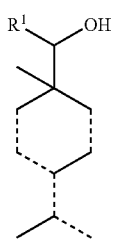

(III)

wherein $R^1$ is a hydrogen atom or a hydrocarbon group having 1 to 4 carbon atoms; and dotted lines each represent a single bond or a double bond with the proviso that both of the adjacent two dotted lines are not double bonds at the same time and that the dotted lines do not include three or more double bonds.

EFFECT OF THE INVENTION

The alcohol compound of the present invention exhibits substantially no woody scent limiting its applications to raw materials of perfume preparations, has a fresh floral odor reminiscent of a natural scent of lily of the valley and an excellent persistency of the fragrance, and is useful as an aromatizing ingredient for toiletry goods, etc. Also, according to the production process of the present invention, since the starting material used therein is inexpensive and stably available, it is possible to produce the alcohol compound of the present invention at low costs.

DETAILED DESCRIPTION OF THE INVENTION

Alcohol Compound

The alcohol compound of the present invention is represented by the general formula (I):

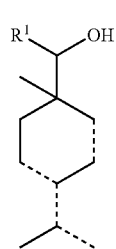

(I)

wherein $R^1$ is a hydrogen atom or a hydrocarbon group having 1 to 4 carbon atoms; and any one of dotted-lines represents a double bond, and the remaining three dotted lines each represent a single bond.

Examples of the preferred hydrocarbon group as $R^1$ include an alkyl group having 1 to 4 carbon atoms, an alkenyl group having 1 to 4 carbon atoms, and an alkynyl group having 1 to 4 carbon atoms. Specific examples of the alkyl group having 1 to 4 carbon atoms include methyl, ethyl, n-propyl, isopropyl, n-butyl, isobutyl and sec-butyl. Specific examples of the alkenyl group having 1 to 4 carbon atoms include vinyl, allyl, 1-butenyl and 1-methyl vinyl. Specific examples of the alkynyl group having 1 to 4 carbon atoms include ethynyl, 2-propynyl and prop-2-yn-1-yl.

Among these groups as $R^1$, preferred are a hydrogen atom, methyl, ethyl, n-propyl, isopropyl, n-butyl, isobutyl and sec-butyl, and from the viewpoints of good diffusing property and natural-like feel of the resulting perfumes, more preferred is a hydrogen atom.

The alcohol compound represented by the above general formula (I) is suitably incorporated into the perfume composition of the present invention.

The perfume composition of the present invention contains the alcohol compound represented by the following general formula (III) including the alcohol compound represented by the above general formula (I), preferably the alcohol compound represented by the above general formula (I), singly, or is obtained by mixing two or more kinds of these alcohol compounds with each other.

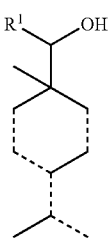

(III)

In the general formula (III), $R^1$ is the same as defined above, and the dotted-lines each represent a single bond or a double bond with the proviso that both of the adjacent dotted-lines are not double bonds at the same time and that the dotted lines do not include three or more double bonds.

[Process for Producing Alcohol Compound: Synthesis of Compound of General Formula (II)]

The alcohol compound represented by the general formula (I) according to the present invention is obtained, for example, by subjecting the alcohol compound represented by the general formula (II) to reduction reaction. The alcohol compound represented by the general formula (II) may be produced, for example, by the method as described in "The Journal of Organic Chemistry", Vol. 32, pp. 3986 to 3989 (1967).

More specifically, as shown in the following reaction formula (A), the alcohol compound represented by the general formula (II) may be produced by reacting 1-isopropyl-4-methyl-1,3-cyclohexadiene represented by the general formula (IV) with an aldehyde in the presence of an acid catalyst to obtain an acetal represented by the general formula (V), and then decomposing the resulting acetal in the presence of the acid catalyst.

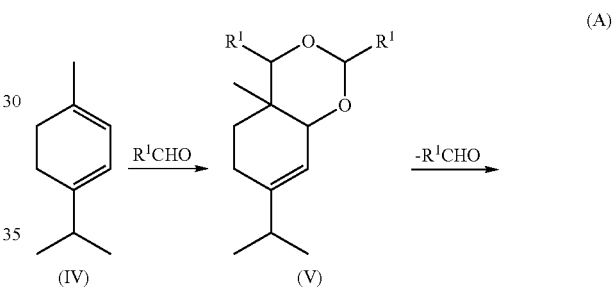

(A)

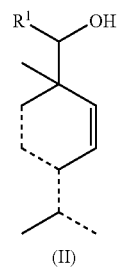

(II)

In the reaction formula (A), $R^1$ and the dotted lines are the same as those in the general formula (II).

The compound represented by the general formula (IV) which is used as the starting material in the reaction formula (A) is inexpensive and stably available. Therefore, according to the production process of the present invention, the alcohol compound of the present invention can be produced at low costs. In addition, as shown in the following reaction formula (B), the alcohol compound represented by the general formula (II) may also be produced by reacting 1-isopropyl-4-methyl-1,3-cyclohexadiene represented by the general formula (IV) with an aldehyde in the presence of an acid catalyst and a carboxylic anhydride to obtain a carboxylic acid ester (VI), and then subjecting the resulting carboxylic acid ester (VI) to hydrolysis in the presence of an acid or base catalyst.

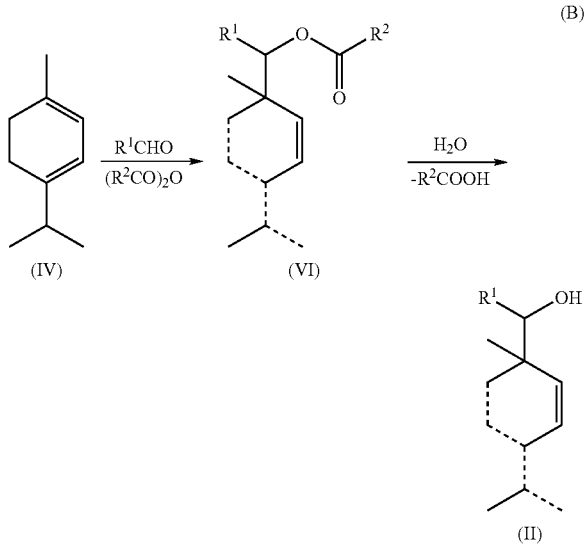

In the reaction formula (B), $R^1$ and the dotted lines are the same as those in the general formula (II); $R^2$ is a hydrocarbon group having 1 to 4 carbon atoms which is the same as defined for $R^1$.

[Process for Producing Alcohol Compound: Synthesis of Compound of General Formula (I)]

The alcohol compound represented by the general formula (I) according to the present invention may be produced, for example, by subjecting the alcohol compound represented by the general formula (II) to reduction reaction as shown in the following reaction formula (C).

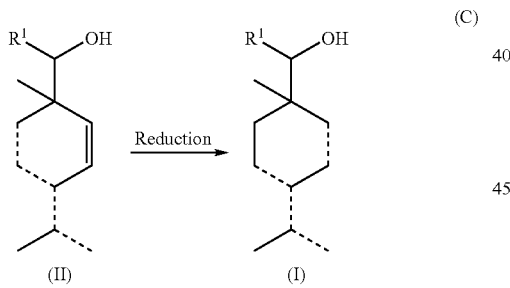

In the reaction formula (C), $R^1$ and the dotted lines in the general formulae (I) and (II) are the same as defined above.

The partial reduction reaction as shown in the reaction formula (C) is preferably carried out using hydrogen in the presence of a catalyst containing at least one metal selected from the group consisting of metals belonging to Groups 8 to 11. The reaction pressure is usually from 0.01 to 10 MPa, preferably from 0.05 to 3 MPa and more preferably from 0.1 to 2 MPa, and the reaction temperature is usually from 0 to 200° C. and preferably from 20 to 150° C.

Specific examples of the metals belonging to Groups 8 to 11 include iron, cobalt, nickel, copper, ruthenium, rhodium, palladium, silver, osmium, iridium, platinum and gold. Among these metals, preferred are iron, cobalt, nickel, copper, ruthenium, rhodium, palladium, osmium, iridium and platinum, and more preferred are rhodium, palladium and platinum.

The configuration of the catalyst used in the above reaction is not particularly limited. The catalyst used is preferably in the form of a supported catalyst obtained by supporting the above metal on a carrier such as carbon, alumina, silica, titania and zeolite. The amount of the metal supported on the carrier is preferably from 0.1 to 20% by mass and more preferably from 0.5 to 10% by mass.

The amount of the catalyst used in the reaction is not particularly limited. The catalyst is used in an amount of preferably from 0.01 to 10% by mass and more preferably from 0.5 to 5% by mass on the basis of the alcohol compound represented by the general formula (II) as the raw material.

The amount of hydrogen consumed during the reaction is preferably from 0.5 to 1.5 moles and more preferably from 0.5 to 1.25 moles per 1 mole of the alcohol compound represented by the general formula (II) as the raw material. Meanwhile, the amount of hydrogen consumed during the reaction is the value obtained by measuring an inner volume of a closed container used in the reaction and a difference in internal pressure therein between before and after the reaction, and then making a calculation from these measured values according to an equation of state of an ideal gas.

The above reduction reaction may be carried out without using a solvent. However, the reaction may also be carried out in a solvent such as methanol, ethanol, isopropyl alcohol, hexane and tetrahydrofuran.

[Process for Producing Alcohol Compound: Synthesis of Compound of General Formula (VII)]

The alcohol compound represented by the general formula (III) includes the alcohol compound represented by the general formula (VII) which is the compound of the general formula (III) in which all of the dotted lines are single bonds.

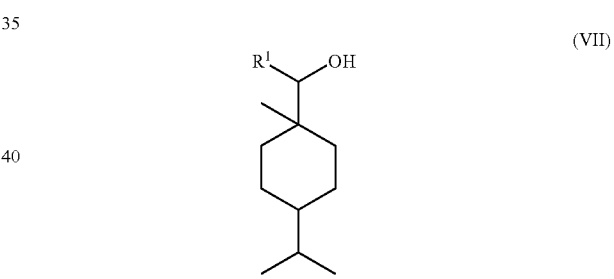

In the general formula (VII), $R^1$ is the same as defined above.

The alcohol compound represented by the general formula (VII) is may be produced, for example, by the method as described in "The Journal of Organic Chemistry", Vol. 32, pp. 3986 to 3989 (1967), or by subjecting the alcohol compound represented by the general formula (I) or (II) to reduction reaction. The reduction reaction is preferably carried out in the presence of a catalyst. The catalyst used in the reduction reaction is preferably the same catalyst as used in the reduction reaction (the above reaction (C)) for producing the alcohol compound represented by the general formula (I). The amount of the catalyst used is not particularly limited, and is preferably from 0.01 to 10% by mass and more preferably from 0.05 to 5% by mass on the basis of the alcohol compound represented by the general formula (I) or (II) as the raw material.

The reaction pressure and reaction temperature are the same as those conditions used in the above reaction (C).

The amount of hydrogen consumed in the reaction is preferably from 0.5 to 3 moles and more preferably from 0.75 to 2 moles per 1 mole of the alcohol compound represented by the general formula (I) as the raw material, and is preferably from 1.25 to 4 moles and more preferably from 1.5 to 3 moles per 1 mole of the alcohol compound represented by the general formula (II) as the raw material. Meanwhile, the amount of hydrogen consumed during the above reaction may be determined by measuring an inner volume of a closed container used in the reaction and a difference in internal pressure therein between before and after the reaction, and then making a calculation from these measured values according to an equation of state of an ideal gas.

The above reduction reaction may be carried out without using a solvent. However, the reaction may also be carried out in a solvent such as methanol, ethanol, isopropyl alcohol, hexane and tetrahydrofuran.

The above alcohol compounds represented by the general formulae (I) to (III) and (VII) exhibit substantially no woody scent and have a fresh floral odor reminiscent of a scent of natural lily of the valley, and are excellent in persistency of the fragrance. Therefore, the alcohol compounds may be used singly or in combination of any two or more thereof as aromatizing ingredients for soaps, shampoos, rinses, detergents, cosmetics, spray products, aromatic agents, perfumes and bath agents.

[Perfume Composition]

The perfume composition of the present invention is obtained by mixing and compounding a single kind or two or more kinds of the alcohol compounds represented by the above general formula (III) with other ordinary perfume components or perfume preparations having a desired composition. Among the alcohol compounds represented by the general formula (III), preferred are the alcohol compounds represented by the general formulae (I), (II) and (VII), and more preferred is the alcohol compound represented by the general formula (I).

The amount of the alcohol compound blended in the perfume composition varies depending upon kind of the perfume preparation, kind of fragrance as aimed, intensity of the fragrance, etc., and is preferably from 0.01 to 90% by mass and more preferably from 0.1 to 50% by mass.

Examples of the perfume components that may be used in combination with the alcohol compound of the present invention include natural essential oils, natural extracts or synthesized perfumes such as hydrocarbons, alcohols, phenols, esters, carbonates, aldehydes, ketones, acetals, ethers, nitrites, carboxylic acids and lactones.

EXAMPLES

The present invention will be described in more detail below by reference to the following Examples and Comparative Examples. However, the following Examples are only illustrative and not intended to limit the invention thereto.

(1) Identification of Samples

The structure of the respective alcohol compounds obtained in Examples and Comparative Examples was identified from nuclear magnetic resonance spectrum ($^1$H-NMR and $^{13}$C-NMR) and IR. The nuclear magnetic resonance spectrum was measured in chloroform-d as a solvent using "Mercury 400" available from Varian, Inc., whereas IR was measured using "FT-710" available from Horiba Ltd.

Example 1

Synthesis of
4-isopropyl-1-methylcyclohexa-2,4-dienylmethanol
and
4-isopropylidene-1-methyl-2-cyclohexenylmethanol A flask was charged with 53 g of paraformaldehyde, 160 g of 1-isopropyl-4-methyl-1,3-cyclohexadiene and 269 g of glacial acetic acid, and the contents of the flask were reacted with each other at 100° C. for 25 h. The resulting reaction mixture was cooled to room temperature, and then after adding 200 mL of an ether thereto, the obtained mixture was washed with a saturated sodium chloride solution and concentrated to obtain 257 g of a reaction solution. To 250 g of the thus obtained reaction solution were added 250 g of water and 100 g of a 48% sodium hydroxide solution, and the obtained mixture was reacted at 95° C. for 5 h, followed by cooling the reaction mixture to room temperature. The reaction mixture was extracted with 75 mL of an ether three times, and the extract solution was washed with a saturated sodium chloride solution. Thereafter, the resulting solution was dried by adding magnesium sulfate thereto, filtered and then concentrated to obtain 186 g of an alcohol mixture. After subjecting 180 g of the alcohol mixture to distillation at a pressure of from 300 to 150 Pa and a temperature of from 100 to 130° C. twice, the obtained distillate was purified using a silica gel column (eluant: hexane/ethyl acetate) twice, and then distilled to obtain 2 g of 4-isopropyl-1-methylcyclohexa-2,4-dienylmethanol and 2 g of 4-isopropylidene-1-methyl-2-cyclohexenylmethanol.

The thus obtained 4-isopropyl-1-methylcyclohexa-2,4-dienylmethanol had a fresh citrus-like floral odor reminiscent of a scent of lily of the valley, and was excellent in persistency of the fragrance. The results of identification of the above compound were as follows.

$^1$H-NMR (CDCl$_3$, 400 MHz, δ ppm): 0.97 (s, 3H), 1.00 (d, 6H, J=6.8 Hz), 1.98 (ddd, 1H, J=17.3, 4.4, 1.2 Hz), 2.01 (br, 1H), 2.24 (dq, 1H, J=1.2, 6.8 Hz), 2.30 (ddd, 1H, J=17.3, 4.4, 1.2 Hz), 3.35 (dd, 2H, J=28, 10.4 Hz), 5.36-5.39 (m, 1H), 5.50 (d, 1H, J=9.6 Hz), 5.90 (dd, 1H, J=9.6, 1.6 Hz)

$^{13}$C-NMR (CDCl$_3$, 100 MHz, δ ppm): 21.46 (q), 21.53 (q), 22.86 (q), 32.47 (t), 32.90 (d), 36.35 (s), 69.56 (t), 116.26 (d), 126.05 (d), 132.83 (d), 140.03 (s)

IR (KBr, neat, cm$^{-1}$): 3350, 2958, 1655, 1463, 1034

The thus obtained 4-isopropylidene-1-methyl-2-cyclohexenylmethanol had a floral odor with a fresh marine ozone-like nuance reminiscent of a scent of lily of the valley, and was excellent in persistency of the fragrance. The results of identification of the above compound were as follows.

$^1$H-NMR (CDCl$_3$, 400 MHz, δ ppm): 0.99 (s, 3H), 1.37-1.44 (m, 1H), 1.66-1.72 (m, 1H), 1.73 (s, 3H), 1.77 (s, 3H), 2.29 (br, 3H), 3.77 (dd, 2H, J=33.4, 10.6), 5.39 (d, 1H, J=10.0), 6.46 (d, 1H, J=10.0)

$^{13}$C-NMR (CDCl$_3$, 100 MHz, δ ppm): 19.69 (q), 20.66 (q), 22.91 (t), 23.61 (q), 31.51 (t), 36.98 (s), 70.59 (t), 126.00 (d), 126.71 (s), 127.22 (s), 131.80 (d)

IR (KBr, neat, cm$^{-1}$): 3355, 2918, 1637, 1450, 1103

Example 2

Synthesis of
4-isopropyl-1-methyl-3-cyclohexenylmethanol from
4-isopropyl-1-methylcyclohexa-2,4-dienylmethanol A glass reaction vessel was charged with 5 g of 4-isopropyl-1-methylcyclohexa-2,4-dienylmethanol produced by the same method as used in Example 1, 0.1 g of 5% Pt/C (water content: 55%) and 50 mL of isopropanol, and the contents of the reaction vessel were reacted with each other at a pressure of from 0.1 to 0.3 MPa and a temperature of 30° C. for 2 h. Thereafter, at the time at which the amount of hydrogen consumed reached 0.55 mole per 1 mole of the raw material, the reaction was stopped, and the reaction mixture was filtered to remove the catalyst therefrom, and then concentrated to obtain 5 g of a reaction solution. The resulting reaction solution was purified using a silica gel column (eluant: hexane/ethyl acetate), and then distilled to obtain 1 g of 4-isopropyl-1-methyl-3-cyclohexenylmethanol.

The thus obtained 4-isopropyl-1-methyl-3-cyclohexenylmethanol had a fresh green-like floral odor reminiscent of a scent of lily of the valley, and was excellent in persistency of the fragrance. The results of identification of the above compound were as follows.

$^1$H-NMR (CDCl$_3$, 400 MHz, δ ppm): 0.90 (s, 3H), 0.99 (d, 6H, J=6.8 Hz), 1.35-1.42 (m, 1H), 1.45 (br, 1H), 1.46-1.53 (m, 1H), 1.67-1.74 (m, 1H), 1.88-1.93 (m, 1H), 1.95-1.99 (m, 2H), 2.17 (dq, 1H, J=6.8, 6.8 Hz), 3.35 (dd, 2H, J=21.6, 10.8 Hz), 5.31 (m, 1H)

$^{13}$C-NMR (CDCl$_3$, 100 MHz, δ ppm): 21.84 (q), 21.94 (q), 22.65 (q), 23.20 (t), 31.01 (t), 34.01 (s), 34.46 (t), 35.34 (d), 71.73 (t), 116.69 (d), 142.55 (s)

IR (KBr, neat, cm$^{-1}$): 3350, 2958, 1666, 1039

Example 3

Synthesis of
4-isopropyl-1-methyl-3-cyclohexenylmethanol from
4-isopropylidene-1-methyl-2-cyclohexenylmethanol A glass reaction vessel was charged with 10 g of 4-isopropylidene-1-methyl-2-cyclohexenylmethanol produced by the same method as used in Example 1, 0.05 g of 5% Pd/C (water content: 53%) and 20 mL of isopropanol, and the contents of the reaction vessel were reacted with each other at a pressure of from 0.1 to 0.4 MPa and a temperature of 30° C. for 4.5 h. Thereafter, at the time at which the amount of hydrogen consumed reached 1.2 moles per 1 mole of the raw material, the reaction was stopped, and the reaction mixture was filtered to remove the catalyst therefrom, and then concentrated to obtain 4-isopropyl-1-methyl-3-cyclohexenylmethanol with a yield of 73%.

Examples 4 and 5

Synthesis of
4-isopropyl-1-methyl-3-cyclohexenylmethanol

A glass reaction vessel was charged with 1 g of 4-isopropylidene-1-methyl-2-cyclohexenylmethanol, the catalyst shown in Table 1 and 20 mL of isopropanol, and the contents of the reaction vessel were reacted with each other at a pressure of from 0.2 to 0.3 MPa and a temperature of 25° C. for the time period shown in Table 1. Thereafter, the reaction mixture was filtered to remove the catalyst therefrom, and then concentrated to obtain 4-isopropyl-1-methyl-3-cyclohexenylmethanol. The amount of hydrogen consumed and the yield of the 4-isopropyl-1-methyl-3-cyclohexenylmethanol are shown in Table 1.

TABLE 1

| Examples | Catalyst | Reaction time | Amount of hydrogen consumed | Yield |
|---|---|---|---|---|
| 4 | 5% Pt/C (water content: 55%); 0.02 g | 2 h | 0.5 mol per mol of raw material | 32% |
| 5 | 5% Rh/C (water content: 51%); 0.02 g | 4.5 h | 0.85 mol per mol of raw material | 55% |

Example 6

Synthesis of
4-isopropyl-1-methylcyclohexylmethanol from
4-isopropyl-1-methyl-3-cyclohexenylmethanol A glass reaction vessel was charged with 4 g of 4-isopropyl-1-methyl-3-cyclohexenylmethanol produced by the same method as used in Example 2, 0.1 g of 5% Pd/C (water content: 53%) and 10 mL of isopropanol, and the contents of the reaction vessel were reacted with each other at a pressure of from 0.3 to 0.4 MPa and a temperature of 30° C. for 18.5 h. Thereafter, at the time at which the amount of hydrogen consumed reached 1.0 mole per 1 mole of the raw material, the reaction was stopped, and the obtained reaction mixture was filtered to remove the catalyst therefrom, and then concentrated to obtain 3 g of a reaction solution. The resulting reaction solution was purified using a silica gel column and HPLC (eluant: hexane/ethyl acetate), and then distilled to obtain 0.4 g of cis-4-isopropyl-1-methylcyclohexylmethanol and 1 g of trans-4-isopropyl-1-methylcyclohexylmethanol.

The thus obtained cis-4-isopropyl-1-methylcyclohexylmethanol had a floral odor with a fresh citrus/green-like nuance reminiscent of a scent of lily of the valley, and was excellent in persistency of the fragrance. The results of identification of the above compound were as follows.

$^1$H-NMR (CDCl$_3$, 400 MHz, δ ppm): 0.85 (d, 6H), 0.90 (s, 3H), 1.00 (m, 1H), 1.10 (m, 2H), 1.12 (m, 2H), 1.40 (m, 1H), 1.41 (m, 1H), 1.49 (m, 2H), 1.61 (m, 2H), 3.47 (s, 2H)

$^{13}$C-NMR (CDCl$_3$, 100 MHz, δ ppm): 20.34 (q), 25.56 (t), 27.57 (q), 32.85 (d), 34.85 (t), 34.88 (s), 44.16 (d), 67.55 (t)

IR (KBr, neat, cm$^{-1}$): 3354, 2931, 1454, 1365, 1034

The thus obtained trans-4-isopropyl-1-methylcyclohexylmethanol had a floral odor with a fresh white floral-like nuance reminiscent of a scent of lily of the valley, and was excellent in persistency of the fragrance. The results of identification of the above compound were as follows.

$^1$H-NMR (CDCl$_3$, 400 MHz, δ ppm): 0.87 (d, 6H), 0.89 (s, 3H), 0.97 (m, 1H), 1.16 (m, 2H), 1.17 (m, 2H), 1.39 (m, 2H), 1.43 (m, 1H), 1.55 (m, 2H), 1.83 (s, 1H), 3.26 (s, 2H)

$^{13}$C-NMR (CDCl$_3$, 100 MHz, δ ppm): 20.32 (q), 19.81 (q), 25.23 (t), 33.21 (s), 34.30 (t), 35.50 (s), 44.79 (d), 75.08 (t)

IR (KBr, neat, cm$^{-1}$): 3356, 2925, 1465, 1385, 1043

Example 7 and Comparative Example 1

Formulation Examples Using
4-isopropyl-1-methylcyclohexa-2,4-dienylmethanol

4-Isopropyl-1-methylcyclohexa-2,4-dienylmethanol produced in Example 1 was compounded with the respective components shown in Table 2 to prepare a perfume for products with a floral green-like odor. The numeral values shown in Table 2 indicate part(s) by mass.

TABLE 2

| Components | Example 7 | Comparative Example 1 |
| --- | --- | --- |
| Cis-3-hexenol | 5 | 5 |
| Citronellyl nitrile | 5 | 5 |
| Cyclovertal (tradename of the product available from Kao Corp.) | 10 | 10 |
| Terpineol | 50 | 50 |
| Phenyl ethyl acetate | 50 | 50 |
| Phenyl hexanol | 120 | 120 |
| Methyl dihydrojasmonate | 240 | 240 |
| Tetrahydrolinalool | 100 | 100 |
| Dimethylbenzyl carbinol | 50 | 50 |
| Dimethylbenzyl carbinyl acetate | 50 | 50 |
| Phenyl ethyl alcohol | 100 | 100 |
| Troenan (tradename of the product available from Kao Corp.) | 50 | 50 |
| Phenylethylmethylethyl carbinol | 50 | 50 |
| Cyclopentadecanolide | 20 | 20 |
| Dipropylene glycol | 0 | 100 |
| 4-Isopropyl-1-methylcyclohexa-2,4-dienylmethanol (compound of the present invention) | 100 | 0 |
| Total | 1000 | 1000 |

In the formulation of the perfume preparation with a floral green-like odor as obtained in Comparative Example 1, when using 100 parts by mass of 4-isopropyl-1-methylcyclohexa-2,4-dienylmethanol as the compound of the present invention in place of 100 parts by mass of the dipropylene glycol, there was obtained the perfume preparation with a floral green-like odor which exhibited an increased floral odor with an emphasized sweetness reminiscent of a scent of lily of the valley, and was excellent in persistency of the fragrance.

Example 8 and Comparative Example 2

Formulation Examples Using
4-isopropylidene-1-methyl-2-cyclohexenylmethanol

4-Isopropylidene-1-methyl-2-cyclohexenylmethanol produced in Example 1 was compounded with the respective components shown in Table 3 to prepare a perfume for products with a floral bouquet-like odor. The numeral values shown in Table 3 indicate part(s) by mass.

TABLE 3

| Components | Example 8 | Comparative Example 2 |
| --- | --- | --- |
| Cis-3-hexenol | 5 | 5 |
| Citronellyl nitrile | 5 | 5 |
| Cyclovertal (tradename of the product available from Kao Corp.) | 10 | 10 |
| Nopyl acetate | 40 | 40 |
| Ethyl linalool | 100 | 100 |
| Terpineol | 50 | 50 |
| Phenyl ethyl acetate | 80 | 80 |
| Phenyl hexanol | 200 | 200 |
| Methyl dihydrojasmonate | 400 | 400 |
| Ambrettolide | 10 | 10 |
| Dipropylene glycol | 0 | 100 |
| 4-Isopropylidene-1-methyl-2-cyclohexenylmethanol (compound of the present invention) | 100 | 0 |
| Total | 1000 | 1000 |

In the formulation of the perfume preparation with a floral bouquet-like odor as obtained in Comparative Example 2, when using 100 parts by mass of 4-isopropylidene-1-methyl-2-cyclohexenylmethanol as the compound of the present invention in place of 100 parts by mass of the dipropylene glycol, there was obtained the perfume preparation with a floral bouquet-like odor which exhibited a well-balanced fresh green and musk odor and was further increased in such a odor reminiscent of a scent of lily of the valley, and was excellent in persistency of the fragrance.

Example 9 and Comparative Example 3

Formulation Examples Using
4-isopropyl-1-methyl-3-cyclohexenylmethanol

4-Isopropyl-1-methyl-3-cyclohexenylmethanol produced in Example 2 was compounded with the respective components shown in Table 4 to prepare a perfume for products with a floral green-like odor. The numeral values shown in Table 4 indicate part(s) by mass.

TABLE 4

| Components | Example 9 | Comparative Example 3 |
| --- | --- | --- |
| Cis-3-hexenol | 5 | 5 |
| Citronellyl nitrile | 5 | 5 |
| Cyclovertal (tradename of the product available from Kao Corp.) | 10 | 10 |
| Ethyl linalool | 100 | 100 |
| Terpineol | 50 | 50 |
| Phenyl hexanol | 150 | 150 |
| Methyl dihydrojasmonate | 300 | 300 |
| Dimethylbenzyl carbinol | 40 | 40 |
| Dimethylbenzyl carbinyl acetate | 40 | 40 |
| Phenyl ethyl alcohol | 100 | 100 |
| Dimethylphenylethyl carbinol | 50 | 50 |
| Amber Core (tradename of the product available from Kao Corp.) | 50 | 50 |
| Dipropylene glycol | 0 | 100 |
| 4-Isopropyl-1-methyl-3-cyclohexenylmethanol (compound of the present invention) | 100 | 0 |
| Total | 1000 | 1000 |

In the formulation of the perfume preparation with a floral green-like odor as obtained in Comparative Example 3, when using 100 parts by mass of 4-isopropyl-1-methyl-3-cyclohexenylmethanol as the compound of the present invention in place of 100 parts by mass of the dipropylene glycol, there was obtained the perfume preparation which exhibited a fresh green odor and an emphasized diffusible floral odor reminiscent of a scent of lily of the valley, and was excellent in persistency of the fragrance.

Example 10 and Comparative Example 4

Formulation Examples Using
cis-4-isopropyl-1-methylcyclohexylmethanol

Cis-4-isopropyl-1-methylcyclohexylmethanol produced in Example 6 was compounded with the respective components shown in Table 5 to prepare a perfume for products with a floral bouquet-like odor. The numeral values shown in Table 5 indicate part(s) by mass.

TABLE 5

| Components | Example 10 | Comparative Example 4 |
|---|---|---|
| Ambrettolide | 10 | 10 |
| Cyclovertal (tradename of the product available from Kao Corp.) | 10 | 10 |
| Dimethylbenzyl carbinol | 50 | 50 |
| Ethyl linalool | 100 | 100 |
| Methyl dihydrojasmonate | 400 | 400 |
| Cis-3-hexenol | 5 | 5 |
| Terpineol | 50 | 50 |
| Tetrahydrolinalool | 70 | 70 |
| Citronellyl nitrile | 5 | 5 |
| Phenyl hexanol | 200 | 200 |
| Dipropylene glycol | 0 | 100 |
| Cis-4-isopropyl-1-methylcyclohexylmethanol (compound of the present invention) | 100 | 0 |
| Total | 1000 | 1000 |

In the formulation of the perfume preparation with a floral green-like odor as obtained in Comparative Example 4, when using 100 parts by mass of cis-4-isopropyl-1-methylcyclohexylmethanol as the compound of the present invention in place of 100 parts by mass of the dipropylene glycol, there was obtained the perfume preparation with a floral bouquet-like odor which exhibited an increased fresh floral odor reminiscent of a scent of lily of the valley, and was excellent in persistency of the fragrance.

Example 11 and Comparative Example 5

Formulation Examples Using trans-4-isopropyl-1-methylcyclohexylmethanol

Trans-4-isopropyl-1-methylcyclohexylmethanol produced in Example 6 was compounded with the respective components shown in Table 6 to prepare a perfume for products with a floral sweet-like odor. The numeral values shown in Table 6 indicate part(s) by mass.

TABLE 6

| Components | Example 11 | Comparative Example 5 |
|---|---|---|
| Cyclovertal (tradename of the product available from Kao Corp.) | 10 | 10 |
| Methyl dihydrojasmonate | 400 | 400 |
| Cis-3-hexenol | 5 | 5 |
| Methylphenylethyl carbinol | 100 | 100 |
| Para-tert-butylcyclohexyl acetate | 50 | 50 |
| Phenyl acetaldehyde glyceryl acetal | 100 | 100 |
| Sandalmysole Core (tradename of the product available from Kao Corp.) | 50 | 50 |
| Terpineol | 50 | 50 |
| Tetrahydrolinalool | 130 | 130 |
| Citronellyl nitrile | 5 | 5 |
| Dipropylene glycol | 0 | 100 |
| Trans-4-isopropyl-1-methylcyclohexylmethanol (compound of the present invention) | 100 | 0 |
| Total | 1000 | 1000 |

In the formulation of the perfume preparation with a floral green-like odor as obtained in Comparative Example 5, when using 100 parts by mass of trans-4-isopropyl-1-methylcyclohexylmethanol as the compound of the present invention in place of 100 parts by mass of the dipropylene glycol, there was obtained the perfume preparation with a floral sweet-like odor which exhibited an increased white floral odor reminiscent of a scent of lily of the valley, and was excellent in persistency of the fragrance.

INDUSTRIAL APPLICABILITY

The alcohol compound of the present invention exhibits substantially no woody scent limiting its applications to raw materials of perfume preparations, has a fresh floral odor reminiscent of a natural scent of lily of the valley and an excellent persistency of the fragrance, and is therefore useful as an aromatizing ingredient for toiletry goods. Also, according to the process for producing the alcohol compound according to the present invention, since the starting material used therein is inexpensive and stably available, it is possible to produce the alcohol compound of the present invention at low costs.

The invention claimed is:

1. An alcohol compound represented by the following general formula (I):

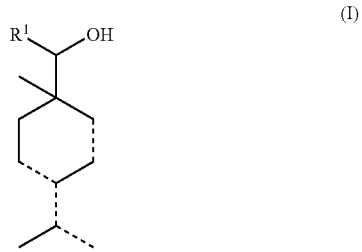

wherein $R^1$ is a hydrogen atom or a hydrocarbon group having 1 to 4 carbon atoms; and any one of dotted lines represents a double bond, and the remaining three dotted lines each represent a single bond.

2. The alcohol compound according to claim 1, wherein $R^1$ in the general formula (I) is a hydrogen atom.

3. A process for producing the alcohol compound represented by the general formula (I) as defined in claim 1, comprising the step of subjecting a compound represented by the following general formula (II) to reduction reaction:

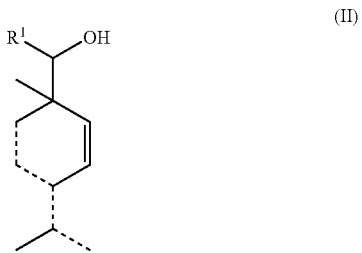

wherein $R^1$ is a hydrogen atom or a hydrocarbon group having 1 to 4 carbon atoms; and any one of dotted lines represents a double bond, and the remaining three dotted lines each represent a single bond.

4. The process according to claim 3, wherein the reduction reaction is carried out in the presence of a catalyst containing at least one metal selected from the group consisting of metals belonging to Groups 8 to 11.

5. A perfume composition comprising an alcohol compound represented by the following general formula (III):

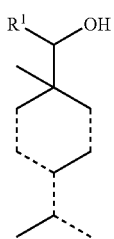 (III)
wherein $R^1$ is a hydrogen atom or a hydrocarbon group having 1 to 4 carbon atoms; and dotted lines each represent a single bond or a double bond with the proviso that both of the adjacent two dotted lines are not double bonds at the same time and that the dotted lines do not include three or more double bonds.
* * * * *